(12) United States Patent
Peterson et al.

(10) Patent No.: US 11,633,603 B2
(45) Date of Patent: Apr. 25, 2023

(54) BURR CAP-MOUNTED ELECTRODES

(71) Applicant: Medtronic, Inc., Minneapolis, MN (US)

(72) Inventors: Erik J. Peterson, Fridley, MN (US); Scott R. Stanslaski, Shoreview, MN (US); Alan Shi, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 36 days.

(21) Appl. No.: 17/136,710

(22) Filed: Dec. 29, 2020

(65) Prior Publication Data
US 2021/0205623 A1    Jul. 8, 2021

Related U.S. Application Data

(60) Provisional application No. 62/957,866, filed on Jan. 7, 2020.

(51) Int. Cl.
| | |
|---|---|
| *A61N 1/00* | (2006.01) |
| *A61N 1/36* | (2006.01) |
| *A61B 5/271* | (2021.01) |
| *A61B 5/293* | (2021.01) |
| *A61N 1/05* | (2006.01) |
| *A61B 5/383* | (2021.01) |
| *A61B 5/00* | (2006.01) |

(52) U.S. Cl.
CPC .......... *A61N 1/36139* (2013.01); *A61B 5/271* (2021.01); *A61B 5/293* (2021.01); *A61B 5/383* (2021.01); *A61B 5/6864* (2013.01); *A61N 1/0534* (2013.01); *A61N 1/0539* (2013.01); *A61B 5/4836* (2013.01)

(58) Field of Classification Search
None
See application file for complete search history.

(56) References Cited

U.S. PATENT DOCUMENTS

| 6,006,124 A | 12/1999 | Fischell et al. |
| 10,780,264 B2 * | 9/2020 | Alam ................ A61N 1/3606 |
| 2005/0075680 A1 * | 4/2005 | Lowry ............... A61N 1/36017 |
| | | 607/45 |
| 2005/0143800 A1 * | 6/2005 | Lando ................ A61N 1/0539 |
| | | 607/116 |

(Continued)

FOREIGN PATENT DOCUMENTS

WO    2009/018426 A1    2/2009

OTHER PUBLICATIONS

Tinkhauser et al., "Directional Local Field Potentials: A Tool to Optimize Deep Brain Stimulation", Wiley Online Library, vol. 33, published online Nov. 18, 2017, 6 pp.

(Continued)

*Primary Examiner* — John R Downey
*Assistant Examiner* — Anant A Gupta
(74) *Attorney, Agent, or Firm* — Shumaker & Sieffert, P.A.

(57) ABSTRACT

A system provides a burr hole cap assembly configured to secure a position of a lead implanted through a burr hole in a cranium of a patient. One or more electrodes are coupled to one or more components of the burr hole cap assembly. The one or more electrode is disposed within the burr hole cap assembly for sensing signals within a brain of the patient or stimulating a portion of the brain of the patient.

20 Claims, 6 Drawing Sheets

(56) References Cited

U.S. PATENT DOCUMENTS

| | | | |
|---|---|---|---|
| 2005/0256541 A1* | 11/2005 | Stypulkowski | A61N 1/05 607/3 |
| 2009/0118804 A1 | 5/2009 | Moffitt et al. | |
| 2009/0203983 A1* | 8/2009 | Carlton | A61N 1/0529 600/378 |
| 2012/0277670 A1* | 11/2012 | Goetz | A61M 25/02 604/93.01 |
| 2014/0074060 A1* | 3/2014 | Imran | A61B 5/24 604/503 |
| 2019/0030321 A1 | 1/2019 | Tinkhauser et al. | |
| 2019/0069927 A1 | 3/2019 | Baxter, III et al. | |
| 2019/0308025 A1* | 10/2019 | Bauer | A61B 17/3468 |

OTHER PUBLICATIONS

Swann et al. "Gamma Oscillations in the Hyperkinetic State Detected with Chronic Human Brain Recordings in Parkinson's Disease", The Journal of Neuroscience, Jun. 15, 2016, 14 pp.

Swann et al., "Adaptive deep brain stimulation for Parkinson's disease using motor cortex sensing", The Journal of Neuroscience, Aug. 1, 2018, 20 pp.

De Hemptinne et al., "Exaggerated phase-amplitude coupling in the primary motor cortex in Parkinson disease", Proceedings of the National Academy of Science, Mar. 19, 2013, 6 pp.

International Search Report and Written Opinion of International Application No. PCT/US2020/067493, dated Apr. 21, 2021, 13 pp.

International Preliminary Report on Patentability from International Application No. PCT/US2020/067493 dated Jul. 21, 2022, 10 pp.

\* cited by examiner

BURR CAP-MOUNTED ELECTRODES

This application claims the benefit of U.S. Provisional Application No. 62/957,866 filed Jan. 7, 2020, the entire content of which is hereby incorporated by reference.

TECHNICAL FIELD

The disclosure relates to burr hole cap assemblies.

BACKGROUND

In some medical systems, a lead (e.g., a lead or a catheter) is implanted in a brain of a patient. The lead may access regions of the brain through a burr hole formed through the patient's skull. A burr hole cap assembly, which is positioned within the burr hole, may be used to retain the position of the lead relative to the burr hole, as well as substantially plug the burr hole.

SUMMARY

This disclosure relates to electrodes in a burr hole cap assembly. As one example, the burr hole cap assembly is used to fixate a deep brain stimulation (DBS) depth lead. Including an electrode in the burr hole cap assembly may reduce implantation procedure time, recording artifacts and invasiveness for cortical-recording based closed-loop DBS.

A system provides a burr hole cap assembly configured to secure a position of a lead implanted through a burr hole in a cranium of a patient. One or more electrodes are coupled to one or more components of the burr hole cap assembly. The one or more electrodes are disposed within the burr hole cap assembly for sensing signals within a brain of the patient or stimulating a portion of the brain of the patient.

In some examples, a first electrode coupled to a base of a burr hole cap assembly receives information indicative of sensed cortical brain activity. The burr hole cap assembly is configured to secure a position of a lead implanted through a burr hole in a cranium of a patient. An 1 MB determines a signal between the first electrode and a second electrode within a brain of the patient and determines whether to adjust therapy based on the determined signal. Therapy can be adjusted based on the determination to adjust therapy.

A system discloses a burr hole base configured for coupling to a cranium of a patient over a burr hole. A cover can substantially cover the burr hole opening and an electrode coupled to the burr hole base can sense signals within a brain of the patient or stimulate a portion of the brain of the patient.

The details of one or more examples are set forth in the accompanying drawings and the description below. Other features, objects, and advantages will be apparent from the description and drawings, and from the claims.

DETAILED DESCRIPTION

Figure 1:
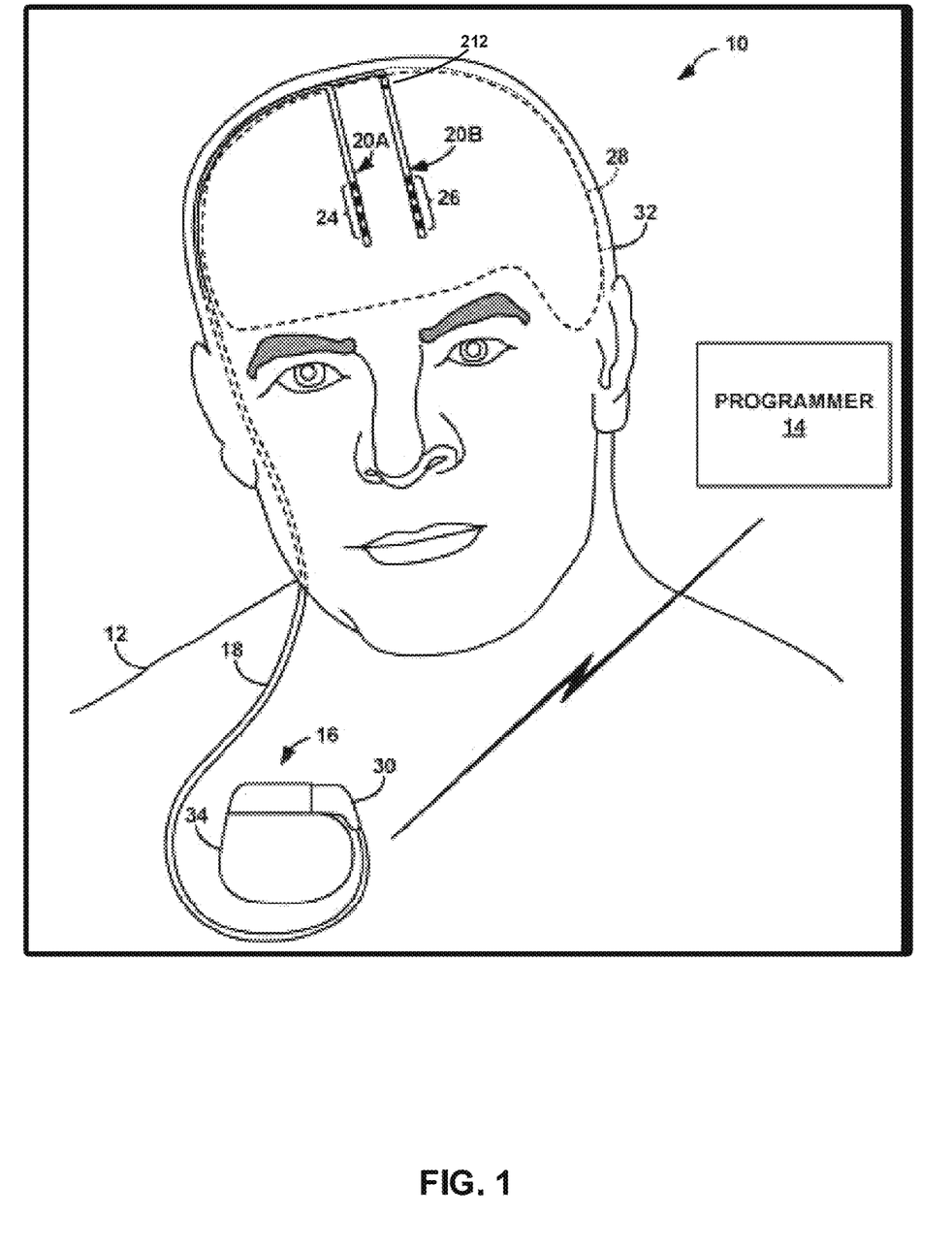
FIG. 1 is a conceptual diagram illustrating an example deep brain stimulation (DBS) system configured to sense a bioelectrical brain signal and deliver electrical stimulation therapy to a tissue site within a brain of a patient.

FIG. 1 is a conceptual diagram illustrating an example therapy system 10 configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to tissue within brain 28, e.g., a tissue site under the dura mater of brain 28 or one or more branches or nodes, or a confluence of fiber tracks. In some examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead 18 is coupled to IMD 16 via connector block 30 (also referred to as a header), which may include, for example, electrical contacts electrically coupling to respective electrical contacts on lead 18. The electrical contacts electrically couple the electrodes 24, 26 carried by leads 20 to IMD 16. Lead 18 traverses from the implant site of IMD 16 within a chest cavity of patient 12, along the neck of patient 12 and through the cranium of patient 12 to access brain 28. IMD 16 can be constructed of a biocompatible material resisting corrosion and degradation from bodily fluids. IMD 16 may comprise a hermetic housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 so electrodes 24, 26 can provide electrical stimulation to target therapy delivery sites within brain 28 during treatment. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MIDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the Circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus. Target therapy delivery sites not located in brain 28 of patient 12 are also contemplated.

Although leads 20 are shown in FIG. 1 as being coupled to a common lead 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In this disclosure, when describing an electrode on housing 34, such disclosure may also apply to cases where housing 34, itself, performs the operation of an electrode. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, and, in the case of electrical stimulation pulses, pulse rate, pulse width, waveform shape, and other appropriate parameters such as duration or duty cycle. In addition, if different electrodes are available for delivery of stimulation, a therapy parameter of a therapy program may be further characterized by an electrode combination, which may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals of patient 12. For example, IMD 16 may include sensing circuitry configured to sense bioelectrical brain signals within one or more regions of brain 28 via a subset of electrodes 24, 26, another set of electrodes (150 (FIG. 2), 206 (FIG. 3), 210, 212 (FIG. 1), or both.

Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals (discussed in greater detail below). In some examples, the sensing circuitry of IMD 16 may sense bioelectrical brain signals via one or more of the electrodes 24, 26 also used to deliver electrical stimulation to brain 28. In other examples, one or more of electrodes 24, 26 may be used to sense bioelectrical brain signals while one or more different electrodes 24, 26 may be used to deliver electrical stimulation.

In accordance with one or more example techniques described in this disclosure, a burr hole cap assembly may be utilized to secure a position of one or both of leads 20A and 20B. This disclosure describes example techniques of leveraging the burr hole cap assembly to include another set of one or more electrodes. For instance, the one or more electrodes may be sensing electrodes used to sense signals in brain 28, may be reference electrodes to one or more sensing electrodes (e.g., sensing electrodes of electrodes 24, 26), and/or may be used for stimulation. Accordingly, as is discussed in greater detail below, electrode(s) can be added to a burr-hole cap assembly or adjacent to a burr-hole cap assembly utilized to fixate the leads 20A, 20B that include DBS electrodes 24, 26.

External medical device programmer 14 is configured to wirelessly communicate with IMD 16 as needed to provide or retrieve therapy information. Programmer 14 is an external computing device the user, e.g., the clinician and/or patient 12, may use to communicate with IMD 16. For example, programmer 14 may be a clinician programmer the clinician uses to communicate with IMD 16 and program one or more therapy programs for IMD 16. In addition, or instead, programmer 14 may be a patient programmer allowing patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) presenting information to the user. In addition, programmer 14 may include a touch screen display, keypad, buttons, a peripheral pointing device or another input mechanism allowing the user to navigate through the user interface of programmer 14 and provide input. If programmer 14 includes buttons and a keypad, the buttons may be dedicated to performing a certain function, e.g., a power button, the buttons and the keypad may be soft keys changing in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device running an application enabling the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs providing efficacious therapy to patient 12 to address symptoms associated with the patient condition. For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors generating signals indicative of motion of patient 12. Programmer 14 may assist the clinician in the creation/identification of therapy programs by providing a system for identifying potentially beneficial therapy parameter values.

In some examples, programmer 14 (or another computing device) is configured to determine, for at least one electrode (e.g., for each electrode 24, 26) of therapy system 10, a therapeutic window, and generate and display information regarding the determined therapeutic windows. For example, programmer 14 may generate a display listing each electrode 24, 26, or a subset of electrodes 24, 26, and, for each electrode, the respective therapeutic window. The therapeutic windows can be displayed as, for example, an efficacy threshold value and an adverse-effects threshold, which may define the boundaries of the therapeutic window in some examples (e.g., X to Y, or X-Y, where X and Y are values for a particular stimulation parameter, such as amplitude). In addition, or instead, the therapeutic windows can be displayed as a magnitude of the difference between the efficacy threshold value and the adverse-effects threshold (e.g., a single number indicating the difference between the efficacy threshold value and the adverse-effects threshold).

As discussed above, the therapeutic windows of electrodes 24, 26 may provide a basis for comparing the potential benefits of each of the electrodes. For example, an electrode associated with a relatively large therapeutic window may indicate the electrode will provide more latitude to find efficacious electrical stimulation parameter values for the patient than another electrode associated with a relatively small therapeutic window. In some examples, the therapeutic windows may be determined based on the actual implantation site of leads 20 within patient 12, i.e., post-operatively, so the information identifying the therapeutic windows for each of the electrodes 24, 26 may be specifically tailored to patient 12. As a result, the therapeutic windows may provide a useful basis for selecting electrode combinations for programming IMD 16.

In some examples, the therapeutic windows may be determined before leads 20 are implanted in patient 12, e.g., pre-operatively. For example, the therapeutic windows may be determined based on the expected implantation site of leads 20 in patient 12. In these examples, the therapeutic windows may be determined based on volume of tissue activation determined using images of patient 12 (e.g., based on a brain atlas specific to patient 12), so the information identifying the therapeutic windows for each of the electrodes 24, 26 may be specifically tailored to patient 12. The target location of leads 20 and electrodes 24, 26 may be selected and modeled, e.g., by a processor of programmer 14, in order to determine the VTAs expected to result from delivery of electrical stimulation by select electrode(s) 24, 26 of leads 20 if leads 20 were implanted in patient 12. In this way, the therapeutic windows may be used to determine at least some electrical stimulation parameter values pre-operatively, prior to implantation of leads 20. In addition, programmer 14 (or another device) may determine the therapeutic windows based on different target locations for electrodes 24, 26, e.g., in order to pre-operatively select an actual implant site for leads 20. Processor 14 may, for example, select the implant site resulting in the relatively largest therapeutic windows or the relatively greatest number of electrodes associated with therapeutic windows greater than or equal to a predetermined size.

Programmer 14 may also be configured for use by patient 12. When configured as a patient programmer, programmer 14 may have limited functionality (compared to a clinician programmer) in order to prevent patient 12 from altering critical functions of IMD 16 or applications detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system. Other combinations or components of system 10 may be possible. For example, rather than IMD 16, a system may include an external medical device coupled to leads similar to leads 24, 26.

During implantation of lead 16 within patient 12, a clinician may attempt to position electrodes 24, 26 of leads 20 close to or within a target anatomical region. The anatomical region within patient 12 serving as the target tissue site for stimulation delivered by IMD 16 may be selected based on the patient condition. For example, stimulating structures of brain 28, such as the Substantia Nigra, may help reduce the number and magnitude of tremors experienced by patient 12. Other anatomical regions for DBS may include the subthalamic nucleus, globus pallidus interna, ventral intermediate, and zona inserta.

With the aid of programmer 14 or another computing device, a clinician may select values for therapy parameters for therapy system 10, including an electrode combination. By selecting electrodes 24, 26 for delivering electrical stimulation therapy to patient 12, a clinician may modify the electrical stimulation therapy to target one or more regions of tissue (e.g., specific anatomical structures) within brain 28 and avoid other regions of tissue within brain 28. In addition, by selecting values for the other stimulation parameter values defining the electrical stimulation signal, e.g., the amplitude, pulse width, and pulse rate, the clinician may generate an efficacious therapy for patient 12 delivered via the selected electrode subset. Due to physiological diversity, condition differences, and inaccuracies in lead placement, the parameter values may vary between patients.

During a programming session, the clinician may determine one or more therapy programs providing effective therapy to patient 12. Patient 12 may provide feedback to the clinician as to the efficacy of the specific program being evaluated, which may include information regarding adverse effects of delivery of therapy according to the specific program. Once the clinician has identified one or more programs beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

As described above, a burr hole cap assembly may include one or more electrodes that can be used for sensing and/or stimulation. Including one or more electrodes in the burr hole cap assembly may provide various benefits and provide for a practical application of sensing and stimulation, as described in more detail.

In some examples, IMD 16 may be configured to receive sensed signals (e.g., sensed from sensing electrodes including those of leads 20A, 20B or included as part of the burr hole cap assembly). IMD 16, based on the received sensed signals, may adjust (e.g., modify) the therapy that IMD 16 provides such as adjusting therapy parameters of a therapy program or selecting a different therapy program. As one example, IMD 16, based on the received sensed signals, may determine that even though therapy is being delivered, brain 28 is still generating signals indicative of a Parkinson's episode. In such examples, IMD 16 may increase the intensity of the therapy (e.g., increase one or more of amplitude, frequency, and pulse width of the therapy) to counteract the activity causing the Parkinson's episode. As another example, IMD 16, based on the received sensed signals, may determine that the therapy is effective, and in response, reduce the intensity of the therapy to conserve power (e.g., reduce one or more of amplitude, frequency, and pulse width). As a later time, patient symptoms may be present again and IMD 16 may receive signals indicative of the patient symptoms and increase the intensity of the therapy in response. As another example, the patient may exhibit characteristics of having overstimulation based on the sensed signals, including increased signal in undesired frequency bands or oscillatory signals, and in response, IMD 16 may reduce the intensity of the therapy.

IMD 16 adjusting the intensity of the therapy based on sensed signals is referred to as closed-loop stimulation. In examples where IMD 16 is providing DBS, one or more of the example techniques described in this disclosure may be related to closed-loop DBS. Accordingly, in closed-loop stimulation systems, there is a feedback signal that IMD 16 uses to adjust the therapy as needed.

In some examples of closed-loop stimulation, including closed-loop DBS, the feedback signal is based on a signal or signals sensed by sensing electrodes. For instance, the feedback signal may be a differential between signals sensed between two different electrodes. As one example, IMD 16 may determine a differential between signals sensed by two sensing electrodes of electrodes 24, and based on the difference between the sensed signals, adjust the therapy (e.g., intensity of the therapy).

However, based on the location of a signal within the brain, the sensed signals may not have sufficient amplitude to allow IMD 16 to determine whether changes are appropriate. For example, based on the location of the signal within the brain (e.g., the signal indicative of patient symptom), it is possible that the signal is sufficiently attenuated when electrodes 24, 26 sense the signal that IMD 16 may not be able to differentiate the signal from noise, and may therefore determine that no adjustment to the therapy is needed.

By having sensing electrodes located in burr hole cap assembly, there may be additional sensing electrodes that can be used to determine whether the patient is symptomatic of his or her condition. For instance, if the signal within the brain is closer to the burr hole cap assembly than electrodes 24, 26, it may be possible for IMD 16 to receive sensed signals of sufficient amplitude to determine that adjustment to therapy is appropriate. Further, in another example, IMD 16 could receive signals from both the implanted sensing electrodes 24 & 26 and the burr hole cap sensing electrodes 150, and although each of the signals may be fairly attenuated, an algorithm could be used to identify the signal more confidently. In another example, the signals could also be used to triangulate the source and/or direction of the sensed signals. The burr hole cap electrodes 150 could be used in signal source triangulation. Adding these signals together could increase the sensed signal, but additional locations could help with determining whether the sensed signal is from one brain structure or another.

Where electrodes are not available in the burr hole cap assembly, some techniques involved placing sensing electrodes, such as for cortical sensing, via a surgical procedure to place such sensing electrodes on the patient's cortex. In such cases, extended procedures or multiple procedures were required: a first procedure to implant leads 20A, 20B through one or more burr holes and a second procedure to place sensing electrodes at different portions.

In the example techniques described in the disclosure, because one or more electrodes are part of the burr hole cap assembly, a separate procedure to place sensing electrodes on the patient cortex may not be needed. For instance, one or more sensing electrodes within the burr hole cap assembly are automatically positioned for sensing (e.g., such as sensing of the cortex) as part of implanting and securing leads 20A, 20B, and a separate procedure may not be needed to position sensing electrodes for such cortical sensing.

In examples discussed below, a burr cap electrode 150 can sense electrical cortical signals. Further, the burr cap electrode 150 can sense any cortical signals resulting from stimulation provided by electrodes 24 and 26. By sensing, the implanting physician can adjust the DBS electrodes 24 and 26 in real time and perform the electrode 24, 26 implantation in one procedure more efficiently than other procedures.

Figure 2:
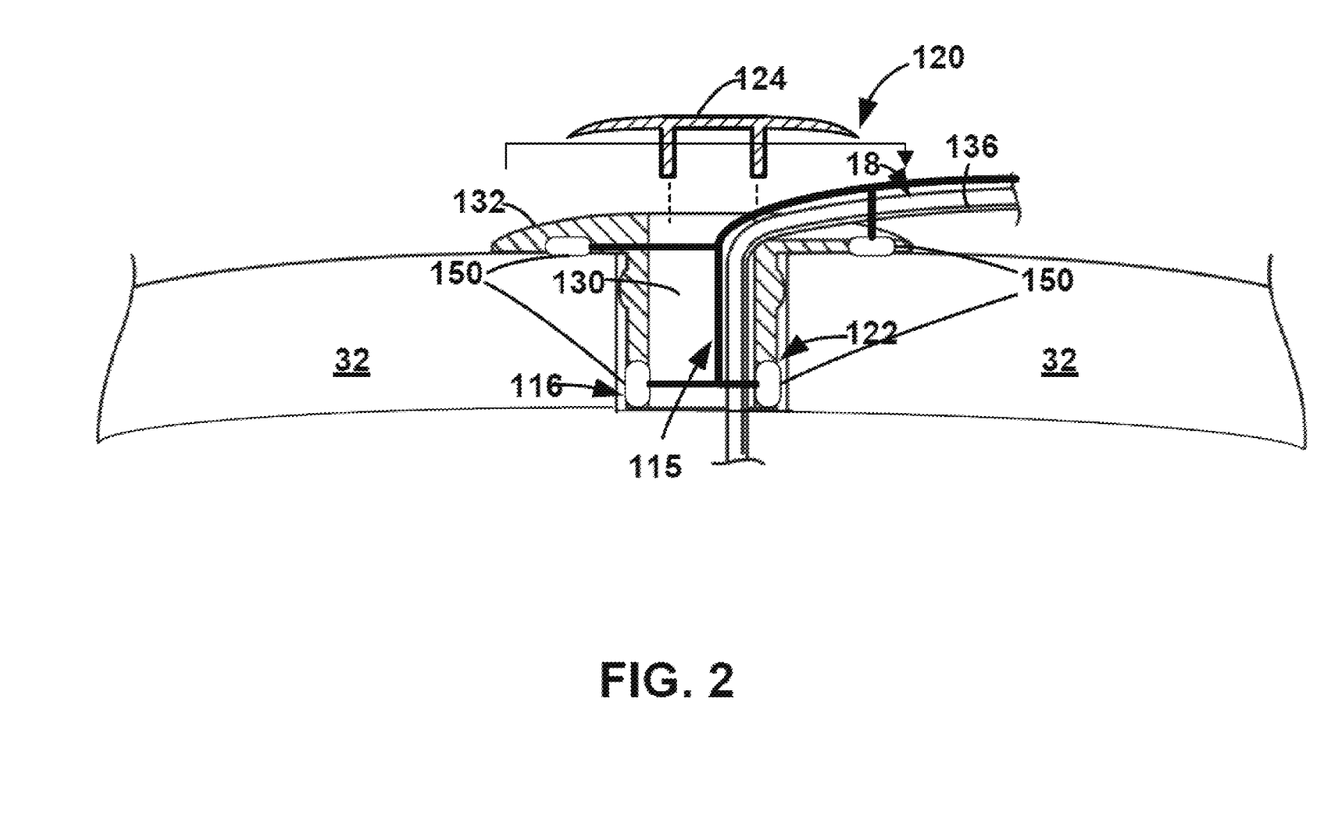
FIG. 2 is a conceptual cross-sectional illustration of a lead extending through a base of a burr hole cap assembly inserted in a burr hole defined through a cranium of a patient.

In the above example, burr cap electrode 150 can be located on the end of base 122 to contact the dura of brain 28. Burr cap electrode 150 may be configured to sense as part of a differential signal. However, in some examples, burr cap electrode 150 may be a reference electrode, such as where the differential signal is measured between one electrode and a reference ground voltage.

For instance, in examples, discussed in detail below, having a reference electrode built into the burr hole cap can provide for reduced-artifact for single-ended DBS recordings when using, the lead extension. As the sensing was performed previously with electrodes closer to, on or part of housing 34, the IMD 16 within the thoracic cavity would often pick up ECG signals which would dampen or make it more difficult to sense cortical signals. This in turn made it harder to determine what was being measured as the cortical effects of electrodes 24 and 26 stimulation was more difficult to determine. Accordingly, in some examples, burr cap electrode 150 may be connected to housing 34, and thereby provide a more proximate reference voltage to ground than housing 34.

Adding a recording electrode to the burr hole cap assembly may require a small modification to a device currently used to fixate the DBS depth lead. In accordance with techniques described in this disclosure, examples discussed below provide for a biomarker access by adding a closed loop-signal source without significant modification to existing DBS implantation procedure. This process can also reduce biologic artifact (e.g., ECG) with improved referencing and thus improved recording. Thus, a burr cap assembly electrode can provide access to therapy control biomarkers through improved recording of cortical sensed brain signals. A biomarker can be a measurable indicator of the severity or presence of some disease state. More generally a biomarker is anything that can be used as an indicator of a particular disease state or some other physiological state of an organism. By improving brain sensing in brain modulation therapies, the implantation time for DBS leads can be significantly reduced.

In FIG. 2, lead 18 extends through opening 130 defined by base 122 of burr hole cap assembly 120 to access a brain 28 of patient 12, which is positioned on the other side of cranium 32 from burr hole cover 124. When cover 124 is installed over base 122 and cover 124 is secured to base 122 (e.g., via a snap fit, an adhesive or any other suitable mechanically fixation), cover 124 helps retain the position of lead 18 relative to burr hole 116. As previously discussed, this may help secure a portion (e.g., a distal portion) of lead 18 configured to deliver therapy to one or more target tissue sites in the brain 28 of patient 12.

Lead 18 may be introduced into patient 12 using any suitable technique. In some examples, a distal end of lead 18 may be guided to a target tissue site within patient 12 (e.g., within the brain 28 of patient 12) with the aid of a stereotactic instrument, which may permit a very precise movement of lead 18 within patient 12. In some of these examples, cover 124 is configured to fit over base 122 while lead 18 is still retained by the stereotactic instrument and held in place relative to the target tissue site via the stereotactic instrument. Upon installation of cover 124 over base 122, cover 124 may substantially fix lead 18 in place relative to burr hole 116; in examples in which lead 18 is relatively rigid, cover 124 may also substantially fix lead 18 at the target tissue site.

In other examples, cover 124 may be configured to fit over base 122 after lead 18 is released from the stereotactic instrument. For example, base 122 may include one or more features substantially fixing the position of lead 18 relative to base 122 prior to installation of cover 124. As an example, groove 133 may be configured to hold a portion of lead 18 retained in groove 133 by friction fit. The clinician implanting lead 18 in patient 12 may introduce lead 18 into groove 133 before or after release of lead 18 from the stereotactic instrument (or other instrument used to implant lead 18). Other techniques may also be used to substantially fix the position of lead 18 relative to base 122 prior to installation of cover 124.

In the example shown in FIG. 2, lead 18 comprises marker 136 corresponding to a specific circumferential location in a known position relative to a therapy delivery feature (e.g., one or more electrodes 20A, 20B or one or more fluid delivery ports) of lead 18. Marker 136 is in a fixed position relative to the outer perimeter of lead 18. Marker 136 is a visual aid used by a clinician to determine the relative rotational orientation between lead 18 and burr hole cap assembly 120, e.g., after lead 18 is implanted in patient 12.

Located underneath of top 132 of base 122 is electrode 150 which is configured to monitor cortical effects of DBS therapy. IMD 16 can adjust the therapy parameters (e.g., increase or decrease stimulation amplitude, pulse width, and/or frequency) in response to sensed cortical values at burr cap electrodes 150. Additional burr cap electrodes 150 can be utilized at varying locations on burr hole cap assembly 120 as shown in FIG. 2. Electrodes 150 can be added to the burr hole cap assembly 120 which is used to fixate the DBS depth lead(s) 20A/20B. It is noted in some examples, electrodes 150 can be recording electrodes. Electrodes 150 can be coupled to the IMD 16 and utilized as a monopolar contact for stimulation and for sensing as needed. Burr hole cap electrodes 150 could be molded into the plastic, or whatever material composing the base 122, with wires 115 running through the cover 124 to a common exit point. The wires 115 would exit, similar to lead 18 and connect to a lead extension back to the IMD 16.

Figure 3:
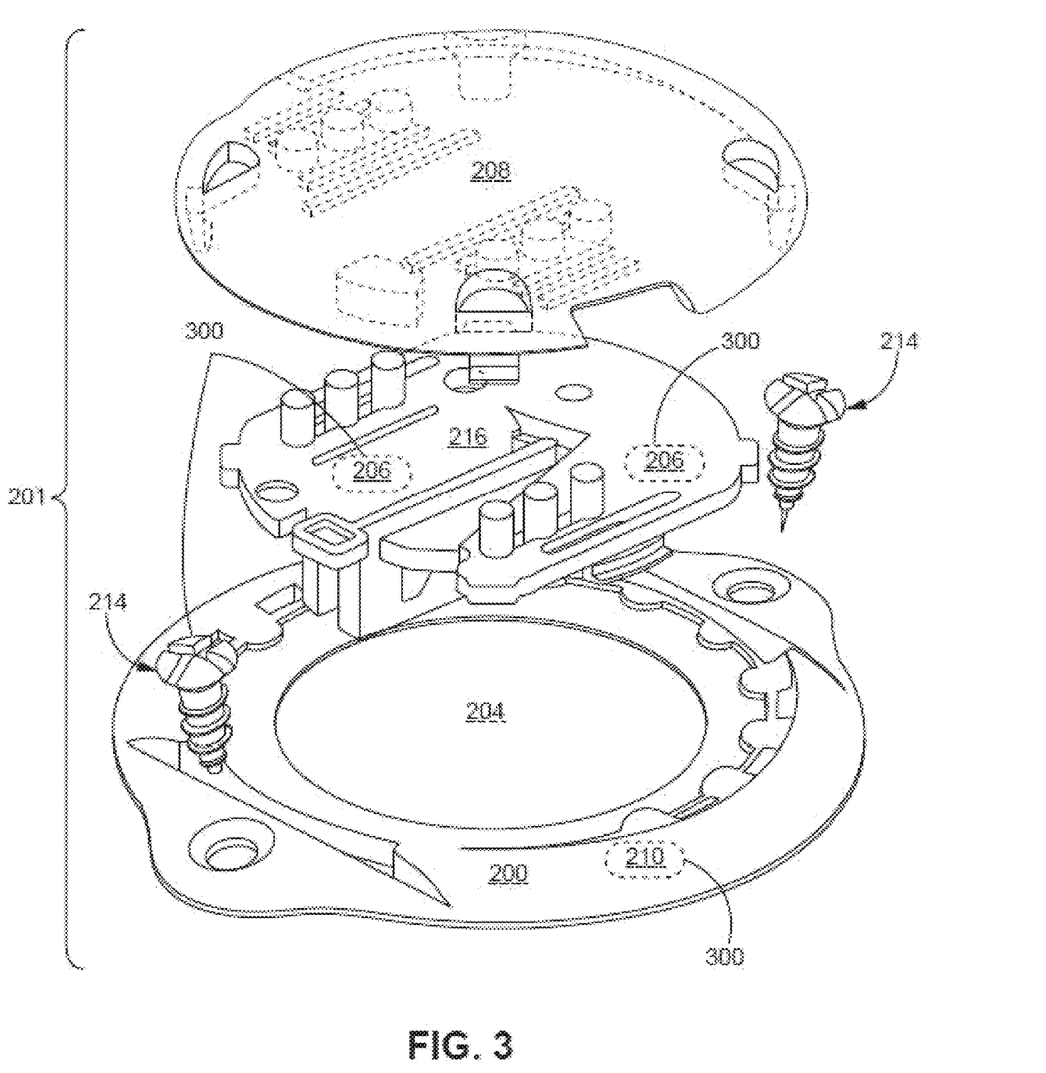
FIG. 3 is an exploded conceptual illustration of a burr cap cover assembly configured to be inserted in a burr hole defined through a cranium of a patient.

With reference to FIG. 3, a burr-hole cap system 201 having a base 200 configured to cover a burr hole 116 in a cranium 32 of a patient 12. The base 200 defines an opening 204 configured to receive a lead 18. A therapy electrode 24, 26 located at a distal end of the lead 20A/20B can be located within a brain 28 of the patient 12. Electrode 206, which is an example of electrode 150, can be operably coupled above the brain 28 at fixed disk 216 for sensing cortical stimulus. A cover 208 can be configured to substantially cover the monitoring electrode 206 and the burr hole 202 surrounded by the base 200. Base 200 can also have a second electrode 210. Electrode 210 could also be at a cortical location detached from base 200, such as electrode 212 shown in FIG. 1, which is located cortically. Each of electrodes 150, 206 and 210 can be connected directly to the housing 34 of the IMD 16 and creates a closed loop reference. For example, each of electrodes 150, 206 and 210 can have a line 300, which runs back to IMD 16 and provides therapy information to IMD 16. IMD 16 can use this information to manipulate the deep brain stimulation for the patient 12. In another example, a physician could choose to use one of these burr hole cap systems 201 with electrodes 206, 210 or 214, implanted to access a different part of the cortex, without using it to fix a depth electrode 24 or 26 in place. In other words, if an application called for depth electrodes 24 and/or 26, more than 2 burr hole caps systems 201 with electrodes 206, 210 and/or 214 could be used to sense other parts of the cortex if desired while still saving procedure time for accessing these parts of the brain.

An IMD 16 can be operably coupled to a proximal end of the lead 20A/20B. Further, the therapy delivery can be modified based upon the sensed cortical stimulus by the monitor electrode 150/206/210/212.

Screws 214 are typically utilized to hold base 200 to the cranium 32 of patient 12. However, crews 214 could also be used as monitoring electrodes for base 200.

Figure 4:
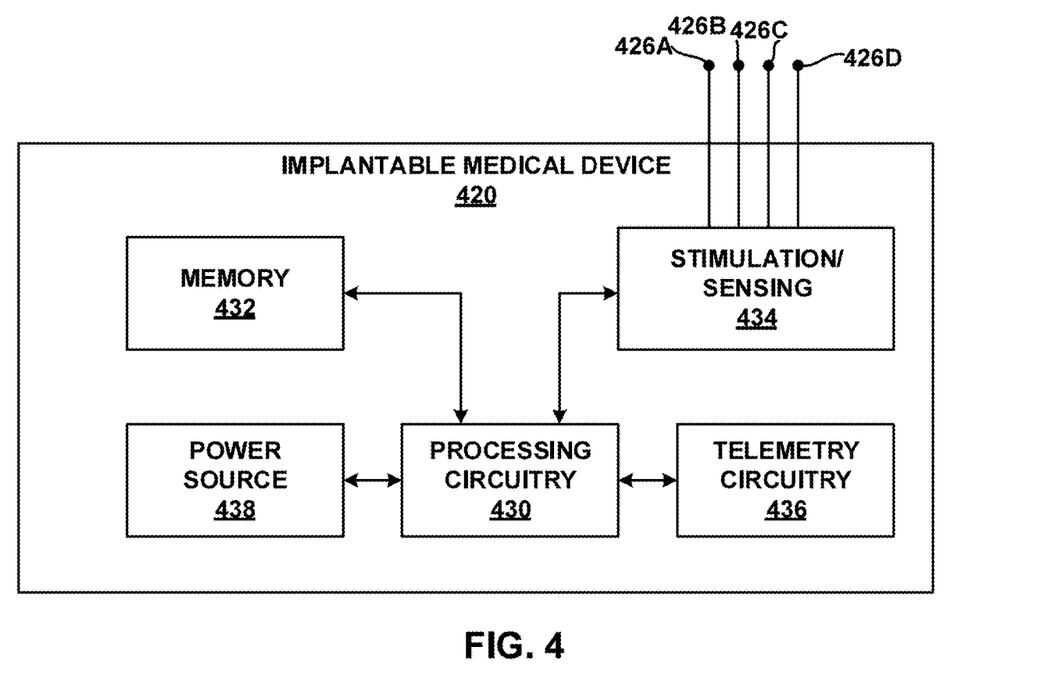
FIG. 4 is a functional block diagram of an example IMD configured to deliver stimulation therapy.

FIG. 4 is a functional block diagram illustrating various components of an example IMD 420. As shown in FIG. 4, IMD 420 includes processing circuitry 430, memory 432, stimulation and sensing circuitry 434, telemetry circuitry 436, power source 438 and other various hardware components providing functionality for operation of the device. For example, IMD 420 includes processing circuitry 430 that may be programmable to be configured to operate according to executable instructions, typically stored in a computer-readable medium or memory 432 such as static, random-access memory (SRAM) device or Flash memory device. IMD 420 may include additional discrete digital logic or analog circuitry not shown in FIG. 4.

Stimulation generator 434 may connect to one or more medical leads 426A-426D. IMD 420 may utilize stimulation generator 434 connected to one or more medical leads 426A-426D to detect and recognize irregularities with the patient requiring treatment and/or therapy based on instructions from processing circuitry 430. In some examples, IMD 420 may utilize stimulation generator 434 connected to one or more medical leads 426A-426D to provide treatment and/or therapy based on instructions from processing circuitry 430.

Telemetry circuitry 436 may comprise any unit capable of facilitating wireless data transfer between IMD 420 and an external programmer 440, where external programmer 440 may comprise an external medical device, a programming device, a remote telemetry station, a physician-activated device, a patient-activated device, a display device or any other type of device capable of sending and receiving signals to and from IMD 420. Telemetry circuitry 436 and external programmer 440 are respectively coupled to one or more antennas for facilitating the wireless data transfer. Telemetry circuitry 436 may be configured to perform any type of wireless communication. For example, telemetry circuitry 436 may send and receive radio frequency (RF) signals, infrared (IR) frequency signals, or other electromagnetic signals. Any of a variety of modulation techniques may be used to modulate data on a respective electromagnetic carrier wave. Alternatively, telemetry circuitry 436 may use sound waves for communicating data or may use the patient's tissue as the transmission medium for communicating with a programmer positioned on the skin of a patient. In any event, telemetry circuitry 436 facilitates wireless data transfer between IMD 420 and external programmer 440.

Power source 438 may be a rechargeable battery, such as a lithium ion or nickel metal hydride battery. Other rechargeable or conventional batteries may also be used. In some examples, external programmer 440 may be configured to recharge IMD 420 in addition to programming IMD 420.

As described herein, in some examples, cortical evoked potentials may be used to determine potentially efficacious therapies for a patient 12. In addition, processing circuitry 430 may control therapy delivery based on monitored cortical evoked potentials (e.g. in a closed-loop or pseudo-closed-loop manner). The processing circuitry 430, can monitor cortical evoked potentials during therapy or stimulation of medical leads 426A, 426B, 426C or 426D, through electrode(s) 150, 200, 212, 206, 210 or 214 and use the cortical evoked potentials as feedback to control subsequent electrical stimulation therapy. For example, in response to detecting cortical evoked potentials above a threshold, processing circuitry 430 may reduce or cease stimulation to conserve power and/or reduce the likelihood of accommodation. As another example, processing circuitry 430 may adjust one or more therapy parameter values defining the electrical stimulation in response to detecting changes to the sensed cortical evoked potentials. In any case, cortical evoked potentials may be monitored for feedback regarding the status or treatment of a target anatomical region instead of directly monitoring the anatomical region with a sensor at or adjacent to the anatomical region.

As discussed above, by adding recording electrodes 150, 200, 206, 210, 212 or 214 to the burr hole cap assembly 120, 201 currently used to fixate the DBS depth lead 20A/20B, procedure time for implantation can be reduced for cortical-recording based closed-loop DBS. Further, reduced invasiveness for cortical-recording based closed-loop DBS can be realized. Reduced-artifact can be realized for single-ended DBS recordings when using a reference electrode 150, 200, 206, 210, 212, 214 built into the burr hole cap assembly 120, 201. Reducing biologic artifact (ECG) with improved referencing improves recording. This provides improved recording, as well as access to therapy control biomarkers. Further, a closed-loop signal source can be provided without significant modification to existing DBS implant procedure.

For example, one example way in which to monitor the efficacy of DBS treatment may be based on a signal difference between one of electrodes 24, 26 and an electrode on housing 34. In such cases, there is a possibility that ECG artifact may obfuscate the sensed signals due to relatively large distance between electrodes 24, 26 and housing 34. With the example techniques described in this disclosure, in examples where one or more of electrodes 150, 200, 206, 210, 212, or 214 is connected to housing 34 (e.g., an electrode in burr hole cap assembly 120, 201 is connected to housing 34), it may be possible to determine a signal difference between electrodes 24, 26 and the electrode in the burr hole cap assembly 120, 201 that is connected to housing 34. Due to the proximity of electrodes 24, 26 and burr hole cap assembly 120, 201, the impact of ECG artifacts or other biopotential noise sources may be minimized.

It should be understood sensing signals using an electrode on housing 34 (which might be housing 34 itself) is still possible and may be utilized in various instances. The above description describes some additional ways in which to sense signals. Moreover, in some examples, the signal may be sensed between electrodes 24, 26, between electrodes 24, 26 and electrodes in burr hole cap assembly 120, 201 (even where the electrodes in burr hold cap assembly 120, 201 are not connected to housing 34), just between electrodes in burr hole cap assembly 120, 201, between electrodes in burr hole cap assembly 120, 201 and the electrode on housing 34, or electrodes 24, 26 and the electrode on housing 34.

Figure 5:
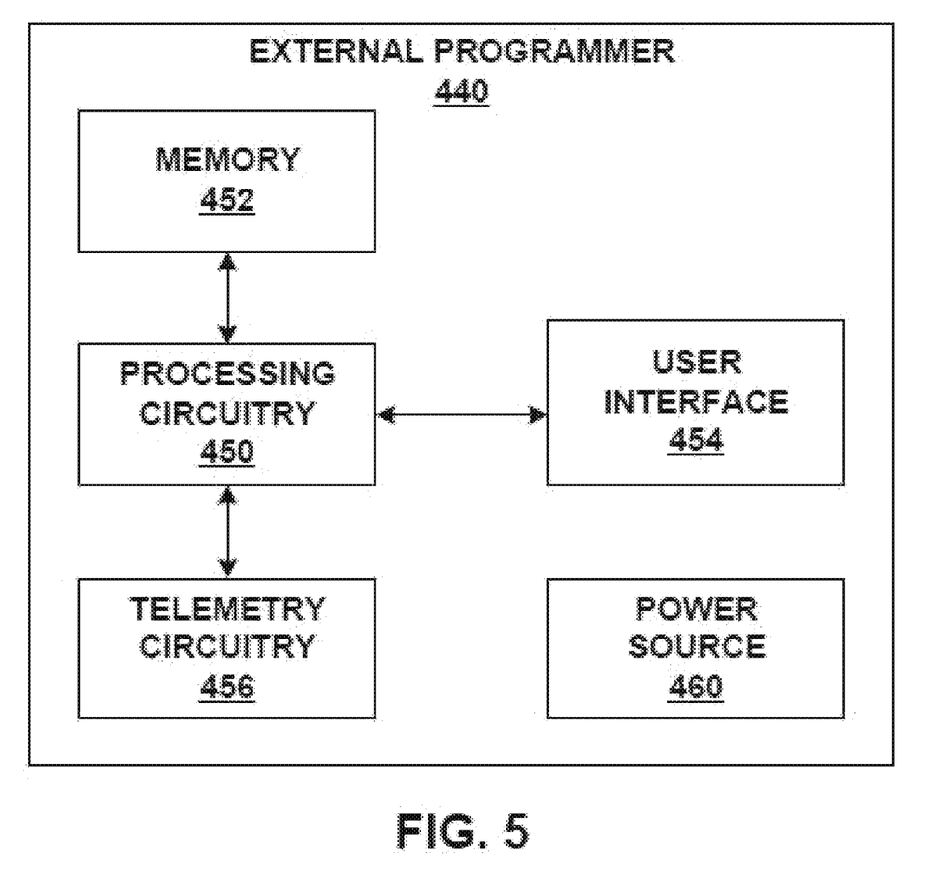
FIG. 5 is a functional block diagram of an example external programmer configured to communicate with the IMD of FIG. 4.

FIG. 5 is a functional block diagram illustrating various components of an external programmer 440 for use with IMD 420. As shown in FIG. 5, external programmer 440 includes user interface 454, processing circuitry 450, memory 452, telemetry circuitry 456, and power source 460. A clinician or patient interacts with user interface 454 in order to manually change the parameters of a therapy program, change therapy programs within a therapy of programs, view therapy information, view historical therapy regimens, establish new therapy regimens, or otherwise communicate with IMD, such as IMD 16 in FIG. 1, or view or edit programming information.

User interface 454 may include a screen and one or more input buttons, allowing external programmer 440 to receive input from a user. Alternatively, or additionally, user interface 454 may additionally, or only, utilize a touch screen display. The screen may be a liquid crystal display (LCD), dot matrix display, organic light-emitting diode (OLED) display, touch screen, or any other device capable of delivering and/or accepting information.

Input buttons for user interface 454 may include a touch pad, increase and decrease buttons, emergency shut off button, and other buttons needed to control the therapy, as described above regarding patient programmer 440. Processing circuitry 450 controls user interface 454, retrieves data from memory 452 and stores data within memory 452. Processing circuitry 450 also controls the wireless transmission of data through telemetry circuitry 456 to an IMD, such as IMD 16 in FIG. 1, by transmitting data to telemetry circuitry 436 as described in FIG. 4. The transmitted data may include therapy program information specifying various drug delivery program parameters. Memory 452 may include operational instructions for processing circuitry 450 and data related to therapy for the patient.

Power source 460 may be a rechargeable battery, such as a lithium ion or nickel metal hydride battery. Other rechargeable or conventional batteries may also be used. In some cases, external programmer 440 may be used when coupled to an alternating current (AC) outlet, i.e., AC line power, either directly or via an AC/DC adapter. In some examples, external programmer 440 may be configured to recharge IMD 420 in addition to programming IMD 420.

Figure 6:
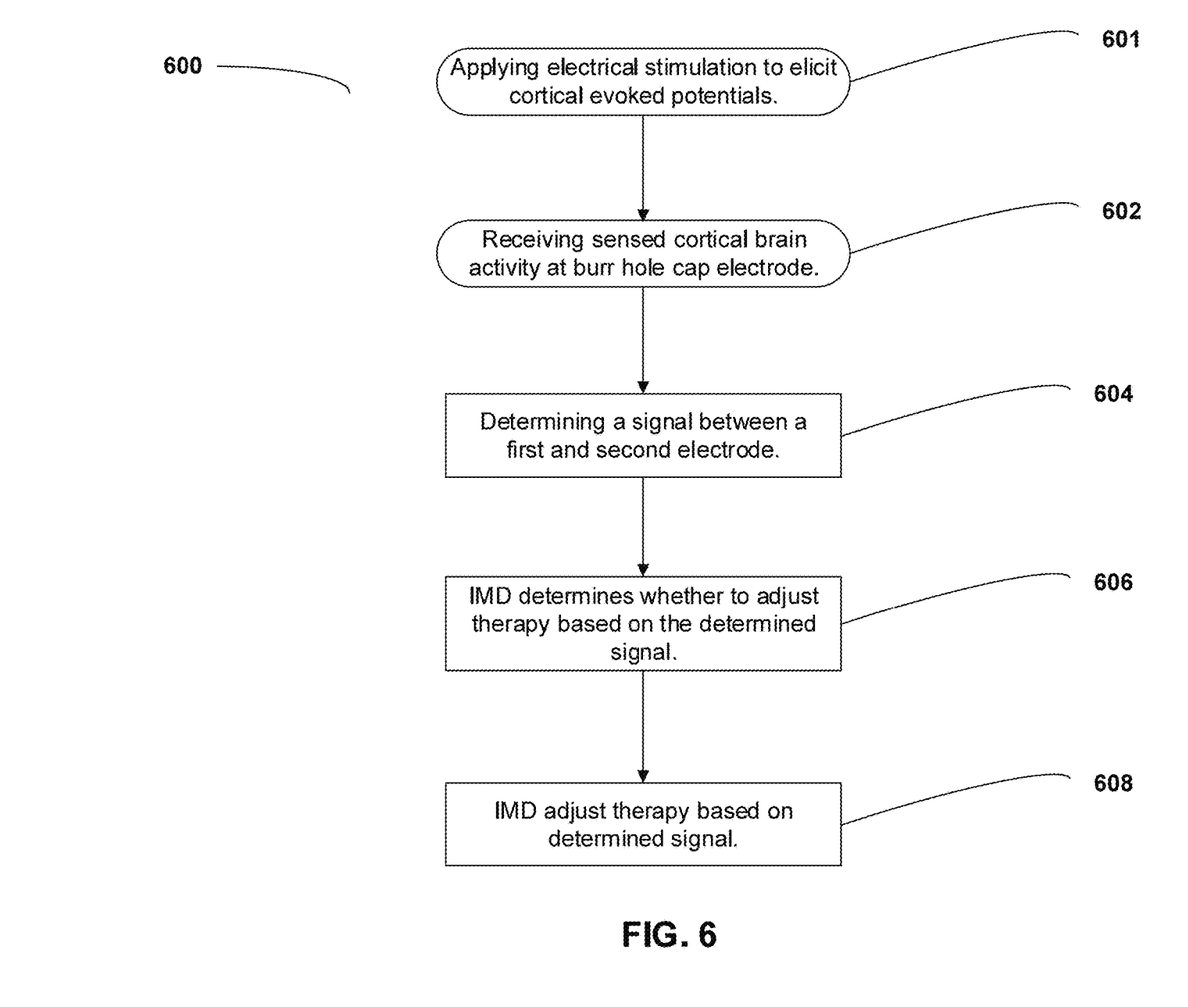
FIG. 6 is a flow diagram of a process for determining DBS therapy utilizing a burr hole cap electrode.

FIG. 6 is a flow diagram of a process for determining DBS therapy utilizing a burr hole cap electrode. Process 600 for determining DBS therapy utilizing a burr hole cap electrode can begin when IMD 16 may apply electrical stimulation to brain 28 to elicit cortical evoked potentials at the same cortex location as the baseline (601).

A first electrode operably coupled to a base of a burr hole cap assembly receives information indicative of sensed cortical brain activity (602). The burr hole cap assembly 120 or 201 can be configured to secure a position of a lead 20 implanted through a burr hole 116 in a cranium 32 of a patient 12.

IMD 16 determines a signal between the first electrode and a second electrode within a brain of the (604). A comparison of the cortical evoked potentials (e.g., sensed via EEG) to the baseline may be indicative of whether or not the patient 12 will respond to electrical stimulation therapy (or other therapy) and, in some examples, whether electrical stimulation will be effective at treating the condition of the patient. For example, if electrical stimulation delivered to the brain 28 elicits cortical evoked potentials greater than the baseline potentials, the electrical stimulation delivered may be effective at treating the condition related to the anatomical. In some examples, the difference between the cortical evoked potentials and the baseline potentials may need to be greater than an efficacy threshold to indicate the patient may respond to the therapy and, in some examples, to indicate the electrical stimulation may be effective in reducing or eliminating the symptoms of the patient's condition. When comparing cortical evoked potentials, one or more characteristics of the cortical evoked potentials may be compared. In other words, comparison of cortical evoked potentials may include comparing respective values of a common characteristic at least partially describing the respective potentials. IMD 16 can determine whether to adjust therapy based on the determined signal (606).

Techniques described in this disclosure utilize sensed cortical evoked potentials from electrodes 150/206/210 and 212 located cortically in the brain 28 of the patient 12 to identify therapies more quickly, or even specific therapy parameter values, likely to reduce or eliminate the symptoms of the patient. A cortical evoked potential can be or include, for example, a response in a cortex of a brain of a patient 12 evoked by the delivery of therapy (e.g., DBS or pharmaceutical agent delivery therapy). A cortical evoked potential can be indicated by, for example, a sensed electrical brain signal (e.g., electroencephalography (EEG) or electrocorticogram (ECoG)).

IMD 16 can then adjust the therapy based on the determination to adjust therapy (608). In other examples, IMD 16 may evaluate, or screen, a plurality of different therapy parameters sets to identify effective electrical stimulation to provide to the patient. For example, the IMD 16 may iteratively deliver electrical stimulation defined by a respective set of therapy parameter values and monitor the resulting sensed cortical evoked potentials. The IMD 16 may select the therapy parameter set evoking a cortical potential exhibiting the relatively largest difference with the baseline potential. In this way, the relatively largest difference between the resulting sensed cortical evoked potentials and the baseline potentials (e.g., between the characteristics of the potentials) may be used as a guideline for selecting an efficacious therapy parameter set for a patient.

The following numbered examples are examples of the systems, devices, and/or techniques described above.

Example 1. A system comprising a burr hole cap assembly configured to secure a position of a lead implanted through a burr hole in a cranium of a patient and one or more electrodes coupled to one or more components of the burr hole cap assembly and disposed within the burr hole cap assembly for at least one of sensing signals within a brain of the patient or stimulating a portion of the brain of the patient.

Example 2. The system of example 1, wherein the burr hole cap assembly comprises a base affixed to the cranium and configured to cover the burr hole in the cranium of the patient, wherein the base defines an opening configured to receive the lead and a fixed disk that couples to the base and is configured to secure the position of the lead.

Example 3. The system of example 2, wherein the one or more electrodes are coupled to the base or the fixed disk.

Example 4. The system of any of examples 2 and 3, wherein the one or more electrodes comprise a plurality of electrodes, wherein a first electrode of the plurality of electrodes is a metallic component that affixes the base to the cranium and a second electrode of the plurality of electrodes is coupled to the fixed disk.

Example 5. The system of any of examples 1-4, wherein the one or more electrodes comprise a first electrode and a second electrode, the system further comprising a medical device configured to receive sensed signals from the first electrode and the second electrode and determine a differential signal between the first electrode and the second electrode.

Example 6. The system of any of examples 1-5, wherein the one or more electrodes comprise at least one electrode coupled to a housing of an implantable medical device.

Example 7. The system of any of examples 1-6, wherein the one or more electrodes comprise pad electrodes.

Example 8. The system of any of examples 1-7, further comprising an implantable medical device configured to receive the sensed signals within the brain from the one or more electrodes and adjust a therapy based on the sensed signals.

Example 9. The system of any of examples 1-8, wherein the one or more electrodes are configured to sense cortical signals.

Example 10. A method comprising receiving information indicative of sensed cortical brain activity that is sensed with a first electrode operably coupled to a base of a burr hole cap assembly, wherein the burr hole cap assembly is configured to secure a position of a lead implanted through a burr hole in a cranium of a patient, determining a signal between the first electrode and a second electrode within a brain of the patient, determining whether to adjust therapy based on the determined signal, and adjusting the therapy based on the determination to adjust therapy.

Example 11. The method of example 10, wherein adjusting the therapy comprises modifying deep brain stimulation based upon sensed cortical electrical signals.

Example 12. The method of any of examples 10 and 11, further comprising applying an electrical stimulation to elicit cortical evoked potentials.

Example 13. A system comprising a burr hole base configured for coupling to a cranium of a patient over a burr hole, a cover configured to substantially cover the burr hole opening, and an electrode operably coupled to the burr hole base, the electrode configured to at least one of sense signals within a brain of the patient or stimulate a portion of the brain of the patient.

Example 14. The system of example 13, further comprising a disk located between the burr hole base and the cover, wherein the disk has a second electrode operably coupled to the disk.

Example 15. The system of any of examples 13 and 14, further comprising a lead passing through the burr hole base and held into place by the cover.

Example 16. The system of example 15, further comprising at least one electrode located at the distal end of the lead for providing deep brain stimulation.

Example 17. The system of example 16, further comprising a proximal end of the lead operably coupled to an implantable medical device.

Example 18. The system of example 17, wherein the implantable medical device is configured to modify the deep brain stimulation based upon signals received from the electrode on the burr hole base.

Example 19. The system of any of examples 13-18, further comprising a plurality of electrodes operably coupled to the burr hole base.

In some examples, the techniques described herein may be used to identify an effective therapy in a relatively short timeframe (e.g., within ten minutes in some cases) of beginning delivery of electrical stimulation. For example, the cortical evoked potentials may in some instances be sensed within ten minutes after the beginning of electrical stimulation delivery. Thus, in some examples, sensing and comparing cortical evoked potentials may reduce or eliminate the need to evaluate potential therapies by waiting for voiding events to occur.

Various examples of the disclosure have been described. These and other examples are within the scope of the following claims.

What is claimed is:

1. A system comprising:
 a burr hole cap assembly configured to secure a position of a lead implanted through a burr hole in a cranium of a patient, wherein the burr hole cap assembly comprises:
  a base configured to be affixed to the cranium around the burr hole in the cranium of the patient, wherein the base defines an opening within the base and the opening is configured to receive the lead; and
  a fixed disk that couples to the base and is configured to secure the position of the lead; and
 one or more electrodes coupled to one or more components of the burr hole cap assembly and disposed within the burr hole cap assembly for at least one of sensing signals within a brain of the patient or stimulating a portion of the brain of the patient, wherein at least one of the one or more electrodes is on the base or the fixed disk.

2. The system of claim 1, wherein the one or more electrodes comprise a plurality of electrodes, wherein a first electrode of the plurality of electrodes is a metallic component configured to affix the base to the cranium and a second electrode of the plurality of electrodes is coupled to the fixed disk.

3. The system of claim 1, wherein the one or more electrodes comprise a first electrode and a second electrode, the system further comprising:
 a medical device configured to receive sensed signals from the first electrode and the second electrode and determine a differential signal between the first electrode and the second electrode.

4. The system of claim 1, wherein the one or more electrodes comprise at least one electrode coupled to a housing of an implantable medical device.

5. The system of claim 1, wherein the one or more electrodes comprise pad electrodes.

6. The system of claim 1, further comprising an implantable medical device configured to receive the sensed signals within the brain from the one or more electrodes and adjust a therapy based on the sensed signals.

7. The system of claim 1, wherein the one or more electrodes are configured to sense cortical signals.

8. A method comprising:
 receiving information indicative of sensed cortical brain activity that is sensed with a first electrode on a base of a burr hole cap assembly, wherein the burr hole cap assembly is configured to secure a position of a lead implanted through a burr hole in a cranium of a patient wherein the base defines an opening within the base and the opening is configured to receive the lead;
 determining a signal between the first electrode and a second electrode within a brain of the patient;
 determining whether to adjust therapy based on the determined signal; and
 adjusting the therapy based on the determination to adjust therapy.

9. The method of claim 8, wherein adjusting the therapy comprises modifying deep brain stimulation based upon sensed cortical electrical signals.

10. The method of claim 8, further comprising applying an electrical stimulation to elicit cortical evoked potentials.

11. A system comprising:
 a burr hole base configured for coupling to a cranium of a patient over a burr hole, wherein the burr hole base defines an opening within the burr hole base;
 a cover, separate from the burr hole base, configured to be secured to the burr hole base and configured to substantially cover the opening within the burr hole base; and
 an electrode on the burr hole base, the electrode configured to at least one of sense signals within a brain of the patient or stimulate a portion of the brain of the patient.

12. The system of claim 11, further comprising a disk located between the burr hole base and the cover, wherein the disk has a second electrode on the disk.

13. The system of claim 11, further comprising a lead passing through the opening within the burr hole base and held into place by the cover.

14. The system of claim 13, further comprising at least one electrode located at the distal end of the lead for providing deep brain stimulation.

15. The system of claim 14, further comprising a proximal end of the lead operably coupled to an implantable medical device.

16. The system of claim 15, wherein the implantable medical device is configured to modify the deep brain stimulation based upon signals received from the electrode on the burr hole base.

17. The system of claim 11, further comprising a plurality of electrodes operably coupled to the burr hole base.

18. The system of claim 1, wherein the base is configured to be affixed to the cranium, wherein the base comprises a side for coupling to the cranium, and wherein at least one of the one or more electrodes is on the side of the base that is for coupling to the cranium or the fixed disk.

19. The method of claim 8, wherein the base is configured to be affixed to the cranium, wherein the base comprises a side for coupling to the cranium, and wherein the first electrode is on the side of the base that is for coupling to the cranium.

20. The system of claim 11, wherein the burr hole base comprises a side for coupling to the cranium, and the electrode is on the side of the burr hole base that is for coupling to the cranium.

* * * * *